United States Patent [19]
Dellacherie et al.

[11] Patent Number: 5,110,909
[45] Date of Patent: May 5, 1992

[54] MACROMOLECULAR CONJUGATES OF HEMOGLOBIN, A PROCEDURE FOR THEIR PREPARATION AND THEIR USES

[75] Inventors: Edith Dellacherie, Malzeville; Michèle Leonard, Neuves-Maisons; Daniel Sacco; Claude Vigneron, both of Nancy, all of France

[73] Assignee: Institut Merieux, Charbonnieres/Baines, France

[21] Appl. No.: 340,826

[22] Filed: Apr. 20, 1989

[30] Foreign Application Priority Data

Apr. 20, 1988 [FR] France .................. 88 05240

[51] Int. Cl.$^5$ .................. A61K 35/14; C07K 13/00
[52] U.S. Cl. .................. 530/385; 514/6; 525/54.1
[58] Field of Search .................. 530/385; 514/6; 525/54.1

[56] References Cited
FOREIGN PATENT DOCUMENTS
0140640 5/1985 European Pat. Off. .

Primary Examiner—Howard E. Schain
Assistant Examiner—Susan M. Perkins
Attorney, Agent, or Firm—Fleit, Jacobson, Cohn, Price, Holman & Stern

[57] ABSTRACT

The subject of the invention is a procedure for the preparation of water-soluble macromolecular conjugates of hemoglobin, characterized in that:

in the first step, Z sites are bound to a polymer P, the Z sites containing, on the one hand, at least one negative charge borne for example by sulfate groups and intended to lead to the formation of an ionic linkage with hemoglobin, and containing, on the other hand, at least one carboxylic group for example intended to lead to the formation of a covalent linkage with hemoglobin, then in the second step, the polymer P containing the Z site(s) is made to react with hemoglobin in the oxygenated form in order to form, on the one hand, at least one ionic linkage between at least one of the Z sites borne by the polymer and hemoglobin and, on the other hand, at least one covalent linkage between the same Z site mentioned above borne by the polymer and hemoglobin.

The macromolecular conjugates obtained by this procedure exhibit a lower affinity for oxygen than that of free hemoglobin.

23 Claims, 4 Drawing Sheets

MACROMOLECULAR CONJUGATES OF HEMOGLOBIN, A PROCEDURE FOR THEIR PREPARATION AND THEIR USES

The invention relates to new, macromolecular conjugates, a procedure for their preparation and their uses as transporters of oxygen, particularly in the context of transfusions.

It is known that it is possible to inject an aqueous solution of hemoglobin free of stroma and made isotonic with blood by the intravenous route.

Now, one of the disadvantages experienced with hemogobin is that it does not remain in the circulation but diffuses outside of the vascular system, in particular on account of its small size.

Several procedures have been used to counteract this disadvantage, i.e. to enhance the intravascular persistence of free hemoglobin in the context of its use as blood "substitute" or as filling solute acting as a transporter of oxygen.

For example, hemoglobin has been coupled to water-soluble macromolecules which have been rendered non-toxic, non-antigenic and hemocompatible.

In this way, many examples of hemoglobins modified by being chemically linked to water-soluble polymers have shown that the time during which hemoglobin resides in the organism can be considerably increased.

Among the various polymers used, the most common are the polysaccharides and, in particular, dextran (French patent No. 2.328.478), hydroxyethyl-starch (French patent No. 2.238.478), inulin (European patent application No. 43.675), and polyalkylene glycols, and more especially polyethylene glycol.

However, in all of these cases the hemoglobin thus modified by being directly linked to these polymers possesses oxygen-carrying properties which are poorly suited to their use in blood transfusion.

In fact, it will be recalled that a blood substitute can only play a role equivalent to that fulfilled by native hemoglobin in the interior of erythrocytes to the extent that the adduct it forms with oxygen is reversible, i.e. that it is capable of binding oxygen (the hemoglobin is then in the oxygenated form) but also that it is capable of easily releasing the bound oxygen (the hemoglobin is then in the deoxygenated form).

This property with respect to oxygen is characterized by the curve (called the Barcroft curve) which represents the variation in the amount of oxygen bound per unit mass of the transporter as a function of the partial pressure of oxygen contained in the atmosphere to which the hemoglobin is exposed.

Figure 1:
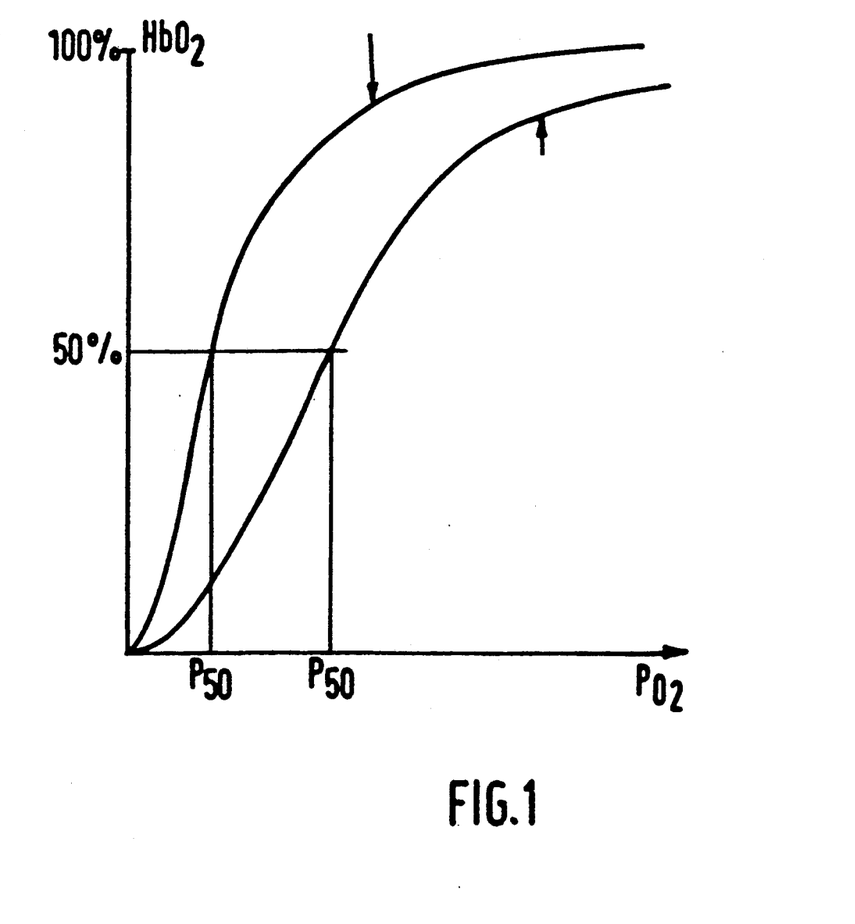
FIG. 1 shows the Barcroft curve of natural hemoglobin and modified hemoglobin of the prior art.

In the case of an aqueous solution of native hemoglobin (concentration 15 $\mu$moles/liter) at pH 7.2 and 25° C., this variation is represented by the reference plot shown in FIG. 1.

One of the parameters associated with this curve is the half-saturation pressure ($P_{50}$) which is the partial pressure of oxygen to which the solution of hemoglobin must be subjected for it to absorb an amount of oxygen equivalent to 50% of the maximal amount with which it is capable of combining. Now, in the case of modified hemoglobin (hemoglobin coupled to polymers) as indicated above, the curve in FIG. 1 showing the percentage of oxygen combined with the hemoglobin at given partial pressures of oxygen is shifted to the left with respect to the curve representing native hemoglobin.

This means that the pressure $P_{50}$ of the modified hemoglobin is lower than that of native hemoglobin; in other words, the modified hemoglobin shows too strong an affinity for oxygen with the disadvantage that the oxygen cannot be returned rapidly to the irrigated tissues.

This change in the oxygen-carrying properties of the modified hemoglobin can be explained in particular by the following reasons:

inside the red cell, native hemoglobin is subject to the influence of 2, 3-diphosphoglycerate (2, 3-DPG) which is the naturally occurring intraerythrocytic effector which binds to the amine groups at the allosteric site of deoxyhemoglobin, leading to a lowering of the affinity of hemoglobin for oxygen.

Improvements to counteract this disadvantage have been suggested in which the coupling between the polymers and the hemoglobin is carried out in the presence of temporary effectors (or ligands) such as 2, 3-diphosphoglycerate or inositol hexaphosphate and in the total absence of oxygen (French patent No. 83.145.45).

These polyphosphated substances complex strongly to the allosteric site of deoxyhemoglobin, thus stabilizing it and protecting the amino groups which are essential for the process of oxygen transport.

However, these effectors are eliminated either during the purification steps of the hemoglobin-polymer conjugates or, it the purification steps have not led to the removal of the effectors, under the dissociating conditions existing in the plasma.

It has been suggested that recourse be had to permanent effectors, for example by coupling pyridoxal-5'-phosphate (Japan Kokai Tokyo JP No. 59.104.323) to counteract this disadvantage.

The use has also been suggested of ligands containing several phosphate groups which, after being bound to hemoglobin, markedly diminish its affinity for oxygen.

However, one of the disadvantages presented by these substances is that their preparation requires at least two, and usually several, operations to be carried out on the hemoglobin and this circumstance leads to the formation of degradation products, in particular methemoglobin.

In the French patent application No. 86.09625, macromolecular conjugates of hemoglobin have also been suggested, the size of which is such that their extravascular diffusion tendency is limited or even reduced to zero, which are protected from the dissociating conditions of the plasma, the oxygen-carrying properties of which are not impaired but enhanced compared with those of free hemoglobin, and the preparation of which entails a limited number of reaction steps on hemoglobin.

Now, these compounds are presented as being obtained by a two-step procedure, namely the binding of Z sites carrying anionic charges to the polymer P, followed by reaction between the polymer P to which the Z sites are bound and hemoglobin in the deoxygenated form in the absence of oxygen.

This procedure, although simplified in comparison with existing procedures, can be difficult to implement on an industrial scale, particularly in the case in which large volumes of solutions of deoxyhemoglobin are used, the difficulty being moreover increased to the extent that it is necessary to work in the absence of oxygen.

Now, the Applicant has found quite unexpectedly a new procedure making it possible, on the one hand, to prepare some of the conjugates which are the subject of the French application No. 86.09625 and, on the other, to extend the access of the person skilled in the art to novel conjugates which possess good oxygen-carrying properties making them suitable for in vivo use as blood substitutes.

In fact, it has turned out that some of the conjugates of hemoglobin can be obtained by using hemoglobin in the oxygenated form and by working under conditions which do not require the absence of oxygen.

Now, the possibility of preparing macromolecular conjugates of hemoglobin by using hemoglobin in the oxygenated form is quite surprising and runs counter to both known data on the conformation of hemoglobin and the results obtained up to the present.

In fact, in view of known data on the conformation of hemoglobin and in particular the fact that in the deoxy form some of the amino groups of hemoglobin participate in locking the conformation of hemoglobin by establishing salt bridges defined below, these amino groups of hemoglobin implicated in the salt bridges are thus unable to react easily with the polymer. When the deoxyhemoglobin and the polymer are coupled in the macromolecular conjugate of hemoglobin obtained, these amine groups then continue to insure the transition of the conformation oxy=deoxy of hemoglobin. Furthermore, deoxyhemoglobin possesses a site ($\beta$ allosteric site) lined with amine functions capable of combining energetically with structures containing anionic groups. Polymers bearing anionic charges will thus react preferentially at this site and if they bear reactive functions such as carboxyl, aldehyde or OH groups, they will react at this site to give conjugates in which the deoxy hemoglobin is stabilized, on the other hand, when the hemoglobin is in the oxygenated form, the salt bridges no longer exist and the corresponding amino groups can then react with the polymer, of whatever kind. The result of this coupling leads to conjugates in which the hemoglobin becomes deoxygenated with difficulty, since the amino groups modified by the polymer can no longer establish the salt bridges which stabilize the deoxy form of hemoglobin. Moreover, the $\beta$ site is very disorganized and the anionic groups of the polymer can no longer exert an orientating effect. Conjugates are thus obtained possessing a very low $P_{50}$.

These hypotheses were confirmed by the results obtained with polymers bearing

Z sites carrying anionic charges constituted by phosphates and/or sulfates, and/or carboxylates and carboxylic, aldehyde or OH groups not situated at the above-mentioned Z sites,
and in which an ionic bond is established between the phosphate and/or sulfate, and/or carboxylate of the Z sites of the polymer and hemoglobin and a covalent bond is established between the carboxyl, aldehyde or OH groups situates on the polymer and hemoglobin.

In fact, when such polymers are made to react with hemoglobin in the oxygenated form, the $P_{50}$ of the macromolecular conjugate of hemoglobin becomes lower than that of native hemoglobin.

Results obtained with polymers bearing carboxylic groups, which on the one hand, as carboxylates, serve as anionic charges which establish ionic linkages between the polymer and hemoglobin, and, on the other, lead to the establishment of covalent links between the polymer and hemoglobin but in which the carboxylic acid groups which are involved in the covalent linkages are not situated in the Z sites which bear the carboxylates which establish the ionic linkages, have demonstrated that the conjugates of hemoglobin prepared from hemoglobin in the oxygenated form possess a $P_{50}$ lower than that of free hemoglobin; in other words, such conjugates of hemoglobin do not have useful oxygen-carrying properties (cf. Preparation Biochemistry 14(4), 313-329 (1984)).

Now, the possibility of preparing conjugates of hemoglobin exhibiting useful oxygen-carrying properties starting from oxygenated hemoglobin has been realised as a result of the procedure of the invention.

Moreover, macromolecular conjugates of hemoglobin have been suggested in which an ionic bond between the polymer and hemoglobin is established between the Z sites of the polymer bearing anionic charges and hemoglobin and a covalent bond is established
  either between the Z sites of the polymer and hemoglobin,
  or between the polymer and hemoglobin, depending on the nature of the anionic charge, the number of anionic charges and the number of monomers.

Now, it has been observed unexpectedly that at least one anionic charge per polymer is sufficient, provided that the anionic charge and the function capable of forming the covalent bond between the polymer and hemoglobin are situated on the same Z site.

One of the aims of the invention is to provide a new procedure making it possible to prepare easily physiologically compatible macromolecular conjugates which are capable of binding oxygen reversibly.

One of the aims of the invention is to provide a new procedure making it possible to prepare easily macromolecular conjugates capable of releasing oxygen more easily than free hemoglobin.

One of the aims of the invention is to suggest a new procedure making it possible to prepare macromolecular conjugates which are easy to synthesize on an industrial scale.

One of the other aims of the invention is to provide a novel procedure making it possible to prepare macromolecular conjugates of hemoglobin by subjecting hemoglobin to not more than two steps, and usually to only one.

Another of the aims of the invention is to suggest a novel procedure making it possible to prepare easily large volumes of aqueous solution containing macromolecular conjugates of hemoglobin which can be used as substitutes for blood, in particular in operations requiring transfusions or the perfusion of an organ.

Another of the aims of the invention is to provide a new procedure making it possible to prepare easily solutions of hemoglobin, the oxygen-carrying properties of which, as characterized by an increase in the $P_{50}$ in vitro compared with free hemoglobin, remain stable in vivo.

Another of the aims of the invention is to suggest a new procedure making it possible to prepare easily macromolecular compounds of hemoglobin exhibiting both a moderate affinity for oxygen and a high hydrodynamic volume, which leads to an enhancement of the intravascular persistence of hemoglobin by suppressing hemoglobinuria during transfusion experiments.

Another of the aims of the invention is to suggest a new procedure making it possible to prepare easily macromolecular conjugates of hemoglobin which exhibit excellent oxygen-carrying properties as revealed by an increase in $P_{50}$ in vitro compared with free hemoglobin, in which the polymer used, when placed in the presence of hemoglobin but not coupled to it, does not necessarily lead to an increase in the $P_{50}$ compared with free hemoglobin.

Another of the aims of the invention is to suggest new macromolecular conjugates exhibiting excellent oxygen-carrying properties as characterized by an increase in the $P_{50}$ in vitro and in which the $P_{50}$ can be adjusted in relation to the number of ionic bonds established between the polymer and hemoglobin.

The procedure for the preparation of water-soluble macromolecular conjugates of hemoglobin, only slightly or not at all biodegradable during the period of time during which the macromolecular conjugate must exercise its oxygen-carrying functions in the plasma, exhibiting an affinity for oxygen less than that of free hemoglobin, characterized in that:

in the first step, Z sites are bound to a polymer P to the extent of at least one Z site per polymer chain, the polymer P being water-soluble, non-toxic, preferably non-antigenic, hemocompatible, of molecular mass of about 1,000 to about 500,000, and preferably of about 1,000 to about 100,000, bearing one or more polar groups, preferably hydroxyl, carboxyl or amino groups, and the Z sites containing, on the one hand, at least one negative charge borne by sulfate and/or phosphate and/or carboxylate groups, and bound to create an ionic bond with hemoglobin, and containing, on the other hand, at least one carboxyl, aldehyde or OH group, intended to create a covalent bond with hemoglobin, either by using a compound Z-Y in which Y is an active function or one which can be activated by means of an activating agent, such as aldehyde, carboxyl, amine, hydroxyl or halogen, or by carrying out a radical reaction at the Z sites on the polymer P;

then in a second step, the polymer P containing the Z site(s) is made to react with hemoglobin in the oxygenated form in a non-deoxygenated medium under conditions such that the hemoglobin does not undergo denaturation and can, after coupling to the polymer, pass reversibly from the oxygenated form to the deoxygenated form in aqueous medium at a pH varying from about 5 to about 9, to give rise, on the one hand, to at least one ionic bond between at least one of the Z sites borne by the polymer and hemoglobin and, on the other, at least one covalent bond between the same Z site mentioned above borne by the polymer and hemoglobin, when the reaction indicated above may lead to imine functions, these latter can be stabilized as amine functions by reduction, for example, with the aid of $NaBH_4$, $NaCNBH_3$, dimethylaminoborane or HCOOH.

For linguistic convenience in the subsequent description and unless indicated otherwise, the expression "Z site" refers to the Z site after binding to the polymer.

In the foregoing and in what follows, the adjective "carboxylate"[is used to designate the anionic charge—derived from a carboxylic acid group—which is implicated in the ionic bond between the polymer and hemoglobin and the adjective "carboxylic" is used to designate the function—also derived from a carboxylic acid group, but different from the previous one—which establishes the covalent linkage between the polymer and hemoglobin.

The adjective "carboxylic" also includes the anhydride formed from two carboxylic acid groups.

Furthermore, the anionic charge derived from a carboxylate may also be derived from an anhydride function.

It has been observed that is was possible to use hemoglobin in the oxygenated form under conditions not requiring the absence of oxygen. More precisely, it has been observed:

that, for example, it is not necessary to deoxygenate in a glove box and to place the solutions used under vacuum in order to dissolve the polymer when the latter has been lyophilized after binding of the Z sites to it;

that it is also unnecessary after deoxygenation of the above-mentioned solutions to bubble nitrogen through them, and that it is also unnecessary to subject the hemoglobin to the steps indicated above, namely, deoxygenation of hemoglobin in a glove box, placing under a vacuum and bubbling nitrogen through it and unnecessary to work subsequently in the absence of oxygen in order to carry out the coupling between the polymer and hemoglobin.

It has also been observed that this procedure can only be applied to the extent that the Z site simultaneously bears:

anionic groups selected from among sulfates, phosphates, carboxylates and carboxylic, aldehyde or OH groups.

In other words, this procedure can only be applied if an ionic bond and a covalent bond are established between the polymer and hemoglobin by the intermediary of at least one give Z site bearing suitable groups.

The procedure of the invention can thus only be applied to the extent that:

an ionic bond has been established between a phosphate, sulfate or carboxylate group, situated at the Z site borne by the polymer and hemoglobin, and the above-mentioned Z site also contains an aldehyde, carboxylic or OH group which forms a covalent bond between the polymer and hemoglobin.

In other words, the process of the invention can only be applied to polymers bearing on the one hand Z sites, carriers of an anionic group selected from sulfate, phosphate, carboxylate and, on the other, carboxylic, aldehyde or OH groups, not located at the above-mentioned Z sites.

In other words, the Z site before being bound to the polymer contains at least three functional groups which are such that:

one of the functions is a function making it possible to attach the Z group to the polymer, one of the functions is a sulfate, phosphate or carboxylate function capable of establishing an ionic bond with an amine of the allosteric site of hemoglobin, one of the functions is an aldehyde, carboxylic or OH function capable of forming a covalent bond with a NH₂ group of hemoglobin.

As activating agent used to activate the Y function of the compound Z-Y which was mentioned above, those selected from the group constituted by the carbodiimides or carbonyldiimidazole may be utilized, for example.

When the Z site is bound to the polymer by means of a radical reaction, a radical initiator is used such as, for example, ceric ammonium nitrate or sulfate or any other agent capable of creating free radicals on the polymer chain (azobis isobutyronitrile, peroxydes, etc. . . . ).

According to an advantageous embodiment of the procedure of the invention, all of the Z sites which are implicated in covalent bonds between the polymer and hemoglobin are the same as the Z sites which are implicated in ionic bonds between the polymer and hemoglobin.

In the procedure according to the invention, if the polar groups of the polymer are ionisable and if they are not all engaged in linkages with the Z sites, these polar groups are preferably blocked in order to prevent subsequent reactions with plasma proteins in vivo.

Thus, when the polar groups are amino groups, those which are not engaged in linkages with the Z sites can be blocked for example by means of acetic anhydride.

When the polar groups are carboxylic acid groups, the latter can be blocked for example by means of ethanolamine.

The procedure of the invention is advantageously carried out under conditions such that the polar groups of the polymer are all involved in linkages with the Z sites, a consequence of which is that the blocking of the polar groups is made superfluous.

These conditions consist in particular in regulating the number of Z sites bound to the polymer in relation to the polar groups of the polymer.

When the polar groups are not already present on the polymer used but are required to be introduced into the polymer, the number of polar groups introduced can also be controlled so that the number of Z sites bound to the polymer is that desired without there being (residual) polar groups to be blocked after binding of the Z sites.

The control of the number of Z sites can be very useful to the extent that it plays a role in the variation of $P_{50}$ through the intermediary of the density of the negative charge resulting from the Z site.

A control of the incorporation of polar groups into the polymer can be carried out in the following manner:

In the example of aminated dextran, the number of amino groups can be modulated by controlling the preceding reaction which consists of reacting epichlorohydrin with dextran in the presence of a catalyst.

This control can be exercised by varying the temperature of the reaction or by varying the amount of catalyst.

Control of the binding of the Z sites to the polar groups of the polymer when the polar groups have already been incorporated into the polymer can be carried out in the following manner:

either by varying the molar ration between the compounds Z-Y defined above and the polar groups of the polymer, or by varying the molar ration between the activating agent defined above and the polar groups of the polymer.

When the Z groups are introduced by a radical reaction, control of their incorporation is carried out independently of the polar groups by modulating the amount of radical initiator used during the radical reaction.

As regards the anionic charge, it has been observed that at least one anionic charge (be it sulfate, phosphate or carboxylate) was sufficient per Z site, and that at least one such Z site was sufficient per polymer.

In other words, it has been observed that the procedure of the invention was applicable to the preparation of conjugates containing at least a single anionic group, and in particular a single anionic group per polymer (this anionic group is not implicated in the covalent coupling between the polymer and hemoglobin), in order to form an ionic linkage between the polymer and hemoglobin.

It has been observed that a necessary condition for the macromolecular conjugates obtained by the procedure of the invention being water-soluble, devoid of toxicity, preferably non-antigenic, and hemocompatible is that the polymers P capable of being incorporated into the structure of the above-mentioned macromolecular conjugates are water-soluble, devoid of toxicity, preferably non-antigenic, and hemocompatible.

It has been observed that the presence in the polymer chain of Z sites, carriers of anionic groups which play the role of permanent effectors, increases the partial pressure at which 50% of the hemoglobin in solution is oxygenated without this effect being attributable to the possible existence of free ligands.

These permanent effectors are such that they also enable hemoglobin to pass reversibly from the deoxygenated form to the oxygenated form with higher stabilization of the conformation of the hemoglobin molecule in the deoxygenated form, which leads to a diminution of the affinity of hemoglobin for oxygen.

In other words, these effectors enable hemoglobin to transport oxygen reversible, and in particular to release oxygen readily in the tissues which are being irrigated.

The covalent linkage is such that it confers on the macromolecular conjugate obtained by the procedure of the invention a stability making it slightly or not at all biodegradable in a plasma medium during the time during which the macromolecular conjugate must exercise its oxygen-carrying functions, i.e. 2 to 3 days, an effect which abolishes extravascular and extrarenal diffusion of the hemoglobin.

In the macromolecular conjugates obtained by the procedure of the invention, the hemoglobin is linked to the polymer by at least one covalent linkage but beyond a critical number of covalent linkages between the polymers and hemoglobin, particularly when this involves the phenomenon of intermolecular cross-linking, this is detrimental to the properties of the hemoglobin.

This critical number of covalent linkages corresponds to the fact that the average molecular mass in weight of the macromolecular conjugates of the invention must not exceed about 1,000,000.

The polymers which are incorporated into the structure of the macromolecular conjugates obtained by the procedure of the invention which are degraded in the plasma have an average molecular mass in weight of about 1,000 to 500,000.

The polymers which are incorporated into the structure of the macromolecular conjugates obtained by the procedure of the invention and which are not degraded in the organism must have an average molecular mass in weight equal to or less than about 10,000, since above this value the polymers pass the renal barrier with difficulty and hence accumulate in the organism.

This is particularly the case for the polyalkylene glycols, polyvinylpyrrolidone, polymethylacrylate and some polysaccharides, which must posses an average molecular mass in weight equal to or less than about 10,000 since they are not biodegradable.

The polymers which are incorporated into the structure of the macromolecular conjugates obtained by the procedure of the invention must be used in a molecular weight range in which they are preferably non-antigenic.

Thus, in the case of dextran, its molecular weight must be lower than about 70,000.

The first step of the preparation of the macromolecular conjugates of the invention and which consists of binding the Z sites to the polymer can be carried out by known methods.

The first step of the preparation of the macromolecular conjugates of the invention can also be carried out by using compounds of the type Z-Y in which Y is an aldehyde, carboxylic, amine, hydroxyl or halogen function. These compounds Z-Y are used by having recourse to standard chemical methods; for example, a benzene penta- or hexacarboxylic acid, 2, 3-diphosphoglyceric acid or pyridoxal-5'-phosphate can be coupled to a polymer which has previously been polyaminated.

In this case it is imperative to remove all traces of the compound Z-Y, for example by desalting on a gel filtration column. In fact, the presence of unreacted compound Z-Y must be avoided since its presence in the macromolecular conjugates of the invention even at low concentrations can lead to false conclusions regarding the properties of the conjugates of the invention.

Recourse may also be had to any other method enabling polyanionic chains to be attached to a polymer, such as a method of radiochemical grafting.

The second step mentioned above is one involving reaction between the polymer and hemoglobin and, if necessary, may be preceded by a step in which the polymer is activated before it is allowed to react with hemoglobin; however, this activation may be carried out almost simultaneously with the reaction between the polymer and hemoglobin.

During the second step the polymer reacts with hemoglobin resulting, on the one hand, in the establishment of the ionic linkages between the Z sites of the polymer and hemoglobin and, on the other, in the formation of the covalent linkages between the polymer and hemoglobin.

In the case in which it is the carboxylic groups of the Z sites which are involved in the covalent linkage with the NH$_2$ groups of hemoglobin, the carboxylic acid groups can be activated by the reagents commonly used in peptide synthesis such as the water-soluble carbodiimides, in particular the hydrochloride of 1-ethyl-3-(3-dimethylaminopropyl) carbodiimide (EDCI), N-hydroxysuccinimide or N-ethoxycarbonyl-2-ethoxy-1, 2-dihydroquinoline (EEDQ).

The linkage formed is thus an amide linkage.

In the case in which it is the aldehyde groups which enter into covalent bond formation with NH$_2$ groups of hemoglobin, recourse may be had to reductive amination, for example.

Reductive amination consists of the condensation of an aldehyde with an amine to form an imine and in the simultaneous reduction of the imine to an amine by means of a reducing agent such as NaBH$_4$, NaCNBH$_3$, dimethylaminoborane or HCOOH.

The linkage thus formed is an amine linkage.

In the case in which it is aldehyde groups of the Z sites which are involved in covalent linkage with NH$_2$ groups of hemoglobin, the reaction may also be carried out under conditions such that the linkage obtained is an amine linkage which can then be stabilized as an amine by reduction with a mild reducing agent such as one of those mentioned above.

When the Z groups contain neither aldehyde groups nor carboxylic groups, but do contain hydroxyl groups, some of which are on adjacent carbon atoms, aldehyde groups can be formed by periodate oxidation for example, in particular with the aid of NaIO$_4$.

The linkage formed between these aldehyde groups and the amino groups of hemoglobin is thus an imine linkage which can be stabilized by reduction to an mine, for example with NaBH$_4$.

When the Z sites contain neither aldehyde groups nor carboxylic groups but do contain one or more OH functions, the Z sites can be made to react with the NH$_2$ groups of hemoglobin with the aid of an appropriate reagent such as carbonyldiimidazole. In this case, the linkage obtained is a carbamate linkage The macromolecular conjugates of hemoglobin in which the covalent linkages with the polymer are imine linkages are not stable in the organism, and it is for this reason that it is appropriate to stabilize the imine function by reducing it to an amine function using NaBH$_4$, NaCNBH$_3$ or dimethylaminoborane.

In the case in which it is necessary to stabilize the covalent linkages, hemoglobin is not subjected to more than two reaction steps and in the other cases, whether polymer P is activated or not, hemoglobin itself is subjected to a single reaction step, a circumstance which is particularly advantageous since a limited number of reaction steps carried out on hemoglobin (two at most) is one of the essential conditions if hemoglobin is not to be denatured and the yield of the reaction is not to be impaired.

During the second step in which the macromolecular conjugate of the invention is formed, it is in fact essential that hemoglobin is not subjected to either serious denaturation or to an appreciable reduction of the relative mobility of the various parts of the molecule in order to preserve, at least in part, its oxygen-carrying properties.

The second step of the reaction is carried out in aqueous medium, buffered or unbuffered, at a pH of between 5 and 9, if required in the presence of an activating agent as indicated above, for a period of time sufficient for reaction to occur but too short for significant amounts of methemoglobin to have formed (higher than about 5%) and at a temperature at which hemoglobin is not denatured.

The aqueous medium is buffered by standard buffers in order to stabilize the pH at the desired value.

The duration of the reaction varies from about 30 min to about 20 h, and advantageously lasts about 1 h to about 8 h at a temperature lying between about 3° and about 30° C.

The duration of the reaction depends particularly on the temperature at which reaction is carried out.

The hemoglobin used is in the oxygenated form and it is advantageous to use a 10% hemoglobin solution.

The ratio of the molar concentrations of polymer and hemoglobin must, in addition, be such that the large majority of the hemoglobin molecules become covalently linked to the polyanionic polymer.

As an example, it may be pointed out that by allowing a mixture of dextran polymer, the average molecular mass in weight of which lies between about 10,000 and 40,000, and hemoglobin to react at a temperature varying from about 3° to 30° C. in solution in an aqueous medium at a pH close to 6.5 and at a ratio of the molar concentrations of dextran to hemoglobin which varies from about 0.5 to about 5, macromolecular conjugates of the invention are obtained which on examination by gel permeation chromatography, for example, reveal no trace of free hemoglobin.

In accordance with an advantageous embodiment of the invention, the procedure of the invention is such that no ionic linkage and no covalent linkage is capable of being formed except between the appropriate groups of the Z sites of the polymer and hemoglobin, respectively.

An advantageous procedure for the preparation of the macromolecular conjugates of the invention is characterized in that the Z sites are attached to the polymer P such that the relationship between the number and nature of the negative charges destined to lead to the formation of an ionic bond between a site and hemoglobin (not involved in linkage between a site and the polymer and not involved in a covalent linkage between a site and hemoglobin) is the following:

when each Z site contains a unique anionic group constituted by a sulfate or a phosphate, there is at least one Z site for every ten monomers of the polymer, When a Z site contains at least two anionic groups, constituted by sulfates and/or phosphates, there is at least one such Z site per polymer chain, when each Z site contains negative charges derived from carboxylates, at least two carboxylate groups—not involved in covalent linkage between the polymer and hemoglobin—must be present at the same Z site, and at least one such Z site must exist for every five monomers, when a Z site contains at least three negative charges derived from carboxylates—not involved in covalent linkage between the polymer and hemoglobin—there is at least one such Z site per polymer chain.

The relationship between the number of Z sites and monomers is statistical to the extent that for example, when it is indicated that there is at least one Z site per polymer chain, this means that some polymer chains may not contain any Z sites and some other chains may contain two sites, but it will be quite obvious that in order to be active with respect to hemoglobin a polymer chain must contain at least one Z site.

According to another advantageous embodiment of the invention, the procedure of the invention for the preparation of macromolecular conjugates is characterized in that the Z sites are bound to the polymer P such that the relationship between the number and nature of the negative charges destined to lead to the formation of an ionic linkage between a site and hemoglobin (not involved in linkage between a site and the polymer and not involved in covalent linkage between a site and the polymer) is the following:

when the Z site contains a unique anionic group constituted by a sulfate or a phosphate, there is at least one such Z site per polymer chain and not more than one Z site for every eleven monomers, when a Z site contains a unique anionic group constituted by a carboxylate—not involved in linkage between the site and the polymer and not involved in covalent linkage between the polymer and hemoglobin—there is at least one such Z site per polymer chain, when a Z site containing two anionic charges derived from two carboxylates—not involved in linkage between the site and the polymer and not involved in covalent linkage between the polymer and hemoglobin—there is at least one such Z site per polymer chain and not more than one such Z site for every six monomers.

The hemoglobin conjugates obtained by the implementation of this variant of the procedure of the invention are new.

According to an advantageous embodiment of the invention, the procedure according to the invention is characterized in that the covalent linkages between the polymer P and hemoglobin are established between at least one carboxylic or aldehyde or OH group borne by the Z sites and at least one amine group of hemoglobin situated at the allosteric site of hemoglobin, in particular the amino group of at least one of the two $\beta$-terminal valines of hemoglobin.

According to an attractive embodiment of the procedure of the invention, the internal salt bridges between the $NH_3^+$ groups and the $COO^-$ groups of hemoglobin remain intact when hemoglobin is in the deoxygenated form.

By salt bridges are meant certain intramolecular bonds which form between $NH_3^+$ ions and $COO^-$ anions when hemoglobin is in the deoxygenated form.

The salt bridges in the macromolecular conjugates obtained by the procedure of the invention must preferably remain intact since if the ions which participate in the formation of these salt bridges are involved in other linkages, the transition of hemoglobin from the oxygenated form to the deoxygenated form occurs with very great difficulty and is incomplete.

The expression "intact salt bridges" means that at least 50% of the salt bridges have not been disrupted and that advantageously 80% to 90% or even 100%, of the salt bridges have not been disrupted.

The criteria used to verify whether the salt bridges are intact are, in particular, the following:

a) The affinity curve for oxygen:

If the affinity curve for oxygen (Barcroft curve) is displaced to the right with respect to that of free hemoglobin, this implies that the salt bridges have not been modified.

b) Hill coefficient (n):

This parameter is an expression for the sigmoidal shape of the Barcroft curve and reflects the degree of cooperativity in the binding of oxygen. The value of n makes it possible to estimate the permanence of the allosteric behaviour of hemoglobin. In the case of native hemoglobin, this coefficient lies between 2.7 and 3.0.

c) Bohr effect:

It consists of determining the oxygen-carrying behaviour of hemoglobin at different pHs which enables the perturbation accompanying the different reaction steps to be evaluated.

According to another attractive embodiment of the invention the macromolecular conjugates of the invention are such that the polymers are selected form among the polysaccharides, in particular among the hydroxylalkyl starches, the alkyl group of which contains 2 to 4 carbon atoms, inulin, dextran and its derivatives, in particular aminated dextran, polyvinyl alcohol, polyvinylpyrrolidone, polymethacrylate and its derivatives, polypeptides, polyalkylene glycols in which the alkylene group contains from 2 to 5 carbon atoms, in particular polyethylene glycol and polypropylene glycol.

The hemoglobin conjugates obtained according to the procedure of the invention are such that the ionic bonds between the polymer and hemoglobin are established between the phosphate, sulfate or carboxylate groups of the Z sites of the polymer and the amine groups of hemoglobin.

According to an attractive embodiment of the invention, the macromolecular conjugates are such that the ionic linkages are established between the carboxylate groups of the Z sites of the polymer and the $NH_2$ groups of hemoglobin.

According to another attractive embodiment of the invention, the Z sites contain $OSO_3H$ or $OPO_3H_2$.

According to another attractive embodiment of the invention, the Z sites are derived from pyridoxalsulfate, epinephrine disulfate, epinephrine trisulfate, norepinephrine disulfate, norepinephrine trisulfate and phenolphtaleine disulfate.

According to another attractive embodiment of the invention, the Z sites are derived from pyridoxal phosphate, adenosine triphosphate, phosphotyrosine, phosphoserine, inositolhexaphosphate and its derivatives, inositol tri-, tetra-, pentaphosphate and their derivatives.

According to another useful embodiment of the invention, the Z sites contain the following groups:

n varies from 1 to 4.

According to another useful embodiment of the invention, the Z site is derived from:
a carboxylic acid containing at least one carboxylate group on the main chain not involved in linkage between the polymer and the Z site and not involved in covalent linkage between the Z site and hemoglobin,
a benzenecarboxylic acid containing at least one carboxylic function not involved in linkage between the polymer and the Z site and not involved in covalent linkage between the Z site and hemoglobin,
a diphospho-2, 3-glycerate group,
citric acid,
1, 2, 3-propane tricarboxylate
or butane tetracarboxylate.

According to another useful embodiment of the invention, Z is derived from 2-hydroxy 5-formyl-phosphoserine benzamide of the formula:

or 4-formyl phosphoserine benzamide of the formula:

The nature of the bond which links Z to the polymer depends on the reactive species present and on the conditions of the reaction.

The linkages through which Z is bound to the polymer are ether, ester, amide or amine linkages.

An ether linkage is formed by a radical grafting with acrylic acid or by the action of chlorosuccinic acid on the OH groups of the polymers; an amide linkage is formed by reaction between the carboxylate groups of the Z groups and the $NH_2$ groups of the polymers; an amine linkage is formed by reaction between the aldehyde groups of the Z groups and the $NH_2$ groups of the polymers, followed by reduction. This last reaction may also be carried out simultaneously with the first: reductive amination.

As illustration, an ester linkage is obtained
by the action of carboxylic groups of a Z site in the form of an anhydride on the OH functions of a polymer,
or by the action of a carboxylic group of a Z site on the OH functions of a polymer in the presence of condensation reagents such as the carbodiimides.

According to an advantageous embodiment of the preparative procedure, the conjugates of the invention in which the Z sites are linked to the polymer by the intermediary of an ester linkage can be obtained in the following manner:

in the first step, the Z sites in which the carboxylic groups are in the form of an anhydride are reacted with the polymer containing OH functions in a medium in which the polymer is soluble in order to bind the Z sites to the polymer;

in the second step, the polymer P containing the Z site(s) is made to react with hemoglobin in the oxygenated form in a non-deoxygenated medium under conditions such that the hemoglobin does not undergo denaturation and can pass, after coupling to the polymer, in a reversible manner from the oxygenated form to the deoxygenated form in aqueous medium at a pH varying between about 5 and about 9, to form, on the one hand, at least one ionic linkage between at least one of the Z sites borne by the polymer and hemoglobin and, on the other, at least one covalent linkage between the same, above-mentioned Z site borne by the polymer and hemoglobin.

According to another advantageous embodiment of the preparative procedure, the conjugates of the invention in which the Z sites are linked to the polymer by the intermediary of an ester linkage can be obtained in the following manner:

in the first step, the Z sites containing carboxylic groups are made to react with the polymer containing OH functions in the presence of a condensing agent such as a carbodiimide in order to bind the Z sites to the polymer;

in the second step, the polymer P containing the Z site(s) is made to react with hemoglobin in the oxygenated form in a non-deoxygenated medium under conditions such that the hemoglobin does not undergo denaturation and can pass, after coupling to the polymer, in a reversible manner from the oxygenated form to the deoxygenated form in aqueous medium at a pH varying between about 5 and about 9, in order to form, on the one hand, at least one ionic linkage between at least one of the Z sites borne by the polymer and hemoglobin and, on the other, at least one covalent linkage between the said above-mentioned Z site borne by the polymer and hemoglobin.

The carbodiimides used depend on the medium in which the polymer is soluble. When the polymer is polyethylene glycol, a carbodiimide soluble in water or in an organic medium can be used. When the polymer is dextran, the carbodiimide used is advantageously the hydrochloride of N'-ethyl-N(3-dimethylaminopropyl) carbodiimide (EDCI) since the polymer is soluble only in water.

As examples of polymers containing OH groups, mention may be made of:

dextran, polyethylene glycol.

By "Z site in which the carboxylic groups are in the form of an anhydride", is meant both the Z sites containing two carboxylic groups in the form of an anhydride (monoanhydrides) and those containing a number of pairs of carboxylic groups in which each pair of carboxylic groups is in the form of anhydride (polyanhydrides: for example, dianhydrides or trianhydrides).

As examples of Z sites in which the carboxylic groups are in the form of anhydrides mention may be made, in addition to the anhydrides of polycarboxylic acids, such as 1,2,4,5-benzene tetracarboxylic acid dianhydride, 1,2,4-benzene tricarboxylic acid anhydride, 1,2,3,4-cyclobutane tetracarboxylic acid dianhydride, benzophenone tetracarboxylic acid dianhydride, the anhydride of aconitic acid as well.

The procedure of the invention advantageously makes use as Z site of the dianhydride of polycarboxylic acid in which one of the carboxylic groups of one of the anhydride functions is involved in covalent linkage between the polymer and hemoglobin, and the other carboxylic groups (including those which arise from the anhydride functions) are useful as ionic link and covalent link between the Z site and hemoglobin.

The procedure of the invention advantageously makes use of the compound of the formula:

or the compound of the formula:

When the polymer is dextran, the medium in which the first step referred to above is carried out is water.

In the case in which the polymer is polyethylene glycol, the medium can be water or an organic medium such as dimethylformamide.

The covalent linkages between the polymer and hemoglobin are established between the $NH_2$ groups of hemoglobin and the carboxylic, aldehyde or OH groups which are found at the Z sites.

The covalent link between the polymer and hemoglobin is an amide, imine, amine or carbamate linkage.

In accordance with a particularly advantageous embodiment of the invention, the covalent linkages are established between carboxylic groups of the Z sites of the polymer and $NH_2$ groups of hemoglobin.

According to an advantageous embodiment of the invention, the procedure of the invention relates to the preparation of hemoglobin conjugates starting from aminated dextran of molecular mass of about 40,000, and about $2.10^{-4}$ moles of benzene hexacarboxylic acid per g of dextran, the ionic linkages being established by the intermediary of the carboxylate groups of the benzene pentacarboxylate bound to the polymer, not involved in linkage between the polymer and the benzene hexacarboxylic acid, and the covalent linkages being established between the other carboxylic groups of the benzene pentacarboxylic acid—implicated in neither the linkage between the benzene hexacarboxylic acid and the polymer nor in the ionic linkages specified above—and the $NH_2$ groups of hemoglobin.

According to an advantageous embodiment of the invention, the procedure of the invention relates to the preparation of hemoglobin conjugates starting from aminated dextran of molecular mass of about 10,000, and about $3.5 \times 10^{-4}$ moles of benzene hexacarboxylic acid per g of dextran.

the ionic linkages being established by the intermediary of the carboxylate groups of benzene pentacarboxylate bound to the polymer, not involved in linkage between the polymer and the benzene hexacarboxylic acid, and the covalent linkages being established between the other carboxylic groups of benzene pentacarboxylic acid—implicated in neither linkage between the benzene hexacarboxylic acid and the polymer nor the ionic linkages specified above—and the $NH_2$ groups of hemoglobin.

According to an advantageous embodiment of the invention, the procedure of the invention relates to the preparation of hemoglobin conjugates starting from aminated dextran of molecular mass of about 10,000, and about $3.2 \times 10^{-4}$ moles of benzene tetracarboxylic acid per g of dextran, the ionic linkages being established by the intermediary of carboxylate groups of the benzene tricarboxylate bound to the polymer, not involved in linkage between the polymer and the benzene tetracarboxylic acid, and the covalent linkages being established between the other carboxylic groups of the benzene tricarboxylic acid—implicated in neither linkage between the benzene tetracarboxylic acid and the polymer nor in the ionic linkages specified above—and the NH$_2$ groups of hemoglobin.

According to an advantageous embodiment of the invention, the procedure of the invention relates to the preparation of hemoglobin conjugates starting from aminated dextran of molecular mass of about 10,000, and about $4 \times 10^{-4}$ moles of butane tetracarboxylic acid per g of polymer, the ionic linkages being established by the intermediary of the carboxylate groups of the butane tricarboxylate bound to the polymer, not involved in linkage between the polymer and the butane tetracarboxylic acid, and the covalent linkages being established between the other carboxylic groups of the butane tricarboxylic acid—implicated in neither linkage between the butane tetracarboxylic acid and the polymer nor in the ionic linkages specified above—and NH$_2$ groups of hemoglobin.

According to an advantageous embodiment of the invention, the procedure of the invention relates to the preparation of hemoglobin conjugates starting from monoamino monomethoxypolyoxyethylene of molecular mass of about 5,000, and about $1.5 \times^{-4}$ moles of benzene hexacarboxylic acid per g of polymer, the ionic linkages being established by the intermediary of the carboxylate groups of the benzene pentacarboxylate bound to the polymer, not involved in linkage between the polymer and benzene hexacarboxylic acid, and the covalent linkages being established between the other carboxylic groups of the benzene pentacarboxylic acid—implicated in neither linkage between the benzene hexacarboxylic acid and the polymer nor in the ionic linkages specified above—and NH$_2$ groups of hemoglobin.

According to an advantageous embodiment of the invention, the procedure of the invention relates to the preparation of hemoglobin conjugates starting from dextran of molecular mass of about 10,000, and about $6.3 \times 10^{-4}$ moles of 1,2,4-benzene tricarboxylic acid per g of polymer, the ionic linkages being established by the intermediary of the carboxylate group of the benzene dicarboxylate bound to the polymer, not involved in linkage between the polymer and the 1,2, 4-1-benzene tricarboxylic acid, and the covalent linkages being established between the other carboxylic group of the benzene dicarboxylic acid—involved in neither linkage between the 1,2,4-benzene tricarboxylic acid and the polymer nor in the ionic linkages specified above—and NH$_2$ groups of hemoglobin.

According to an advantageous embodiment of the invention, the procedure of the invention relates to the preparation of hemoglobin conjugates starting from dextran of molecular mass of about 10,000, and about $1,15 \times 10^{-3}$ moles of 1,2,4,5-benzene tetracarboxylic acid per g of polymer, the ionic linkages being established by the intermediary of the carboxylate groups of the benzene tricarboxylate bound to the polymer, not involved in linkage between the polymer and the 1,2, 4,5-benzene tetracarboxylic acid, and the covalent linkages being established between the other carboxylic groups of the benzene tricarboxylic acid—implicated in neither linkage between the 1,2,4,5-benzene tetracarboxylic acid and the polymer nor in the ionic linkages specified above—and NH$_2$ groups of hemoglobin.

The macromolecular conjugates obtained by the procedure of the invention possess the advantage of being synthesized easily with little or no formation of methemoglobin (less than about 5%) and of involving hemoglobin in only a limited number of reactions which prevents it being denatured.

Moreover, the macromolecular conjugates obtained by he procedure of the invention do not contain effectors of low molecular mass and unbound, which lead in experiments in vitro to an increase of the P$_{50}$, but which can be easily removed by extrarenal or extravascular diffusion during the assays in vivo, and the effect of which is rapidly reduced to zero.

The macromolecular conjugates obtained by the procedure of the invention offer the advantage of having only a moderate affinity for oxygen and of having a large hydrodynamic volume, which leads to an enhancement of the intravascular persistence of hemoglobin by suppression of hemoglobinuria during blood transfusions.

The hemoglobin conjugates irreversibly linked to polyanionic polymers prepared according to the invention can, when they are dissolved in aqueous solutions of suitable composition, play a role as blood substitutes, particularly in operations requiring transfusions or the perfusion of an organ.

Consequently, the invention also relates to aqueous solutions containing the conjugates obtained according to the procedures described above and in particular to solutions made isotonic with blood by prolonged dialysis against a Tyrode solution (composition: NaCl 8 g/l; KCl 0.2 g/l; CaCl$_2$ 0.2 g/l; MgCl$_2$ 0.1 g/l; NaH$_2$PO$_4$ 0.05 g/l; NaHCO$_3$ 1 g/l; D-glucose 1 g/l) for example and concentration by ultrafiltration until a hemoglobin concentration of about 7% is obtained.

Preparations of macromolecular conjugates of hemoglobin obtained by the process according to the invention have been examined as potential transporters of oxygen. It has been possible to show that they are in fact capable of binding oxygen reversibly and, in particular, of releasing it more readily than free hemoglobin as is illustrated by the curves relating to the oxygen affinity of the products described in the Examples 1, 3 and 5 below and presented in FIG. 5 which will be discussed later. In fact, these preparations appear to be characterized by half-saturation pressures (P$_{50}$) which are very high (from 900 to 5,000 Pa) whereas under the same conditions (0.05M NaCl, pH 7, 25° C.) that of native hemoglobin is equal to about 480 Pa.

Thus, these conjugates can be used to supply large amounts of oxygen to ischemic tissues. They may also be used in transfusions and be administered to patients int eh form of an aqueous solution made isotonic with blood, in the presence or absence of excipients. The conjugates can also be lyophilized in the presence or absence of a protecting agent or atomized, and be redissolved in water before utilization.

The macromolecular conjugates obtained by the procedure of the invention have been assayed in mice with respect to the acute toxicity as shown below.

The various polyanionic polymers described in the examples have been injected into mice of the SWISS strain under the following conditions: the polymers were dissolved in distilled water at a concentration included between 2.5 g and 5 g/l and the pH is adjusted to 7.4.

0.5 ml of each solution was then injected by the intraperitoneal route into 5 mice whose behaviour was then kept under observation for a period of seven days. These assays have not revealed any symptons of acute toxicity.

Another subject of the invention is new macromolecular conjugates of hemoglobin, only slightly or not at all biodegradable during the period of time during which the macromolecular conjugate must exercise its oxygen-carrying functions in the plasma, exhibiting an affinity for oxygen less than that of free hemoglobin, characterized in that it is constituted by:

on the one hand, hemoglobin which can pass reversibly from the deoxygenated form to the oxygenated form, on the other, a water-soluble polymer P, non-toxic, preferably non-antigenic, hemocompatible, of molecular mass of about 1,000 to about 500,000, and preferably of about 1,000 to about 100,000, comprising one or more polar groups, preferably hydroxyl, carboxyl or amino groups, this polymer comprises Z sites containing, on the one hand, at least one negative charge borne by at least one group selected form among the following groups: sulfate, phosphate, carboxylate and intended to lead to the formation of an ionic linkage with the polymer and containing, on the other hand, at least one carboxylic, aldehyde or OH group, intended to lead to the formation of a covalent linkage with the polymer, the polymer P being linked to the hemoglobin on the one hand, by the intermediary of at least one ionic linkage established between at least one of the negative charges of the Z sites borne by the polymer P and hemoglobin, and on the other hand, by the intermediary of at least one covalent linkage established between at least one of the carboxylic, aldehyde or OH groups of the above-mentioned Z site borne by the polymer P and hemoglobin, the number of covalent linkages between the polymer and hemoglobin being such that the macromolecular conjugate has a mean molecular mass of about 70,000 to about 1,000,000, and preferably of about 70,000 to about 500,000, the relationship between the number and nature of the negative charges, the number of sites and the number of monomers being as follows:

when a Z site contains a unique anionic group constituted of a sulfate or a phosphate, there is at least one such Z site per polymer chain and not more than one such Z site for every eleven monomers, when the Z site contains a unique anionic group constituted by a carboxylate not involved in linkage between the site and the polymer and not involved in covalent linkage between the polymer and hemoglobin, there is at least one such Z site per polymer chain, when a Z site contains two anionic charges derived from two carboxylates, there is at least one such Z site per polymer chain and not more than one such Z site for every six monomers.

This class of new macromolecular conjugates of the invention is characterized in particular:

by the fact that at least one of the ionic linkages and at least one of the covalent linkages are established with the involvement of suitable groups situated at the same Z site and by the fact that there is at least one single Z site as defined above per polymer chain; in other words, a single Z site as defined above suffices per chain.

It has been observed that this class of new macromolecular conjugates possesses useful oxygen-carrying properties, whereas the macromolecular conjugates of hemoglobin in which the conditions between the nature, the number of anionic charges at a Z site, and the number of Z sites per polymer chain are the same but differ from the conjugates defined above by the fact that the covalent linkage is established between a carboxylic, aldehyde or OH group which is not situated at the Z site (which contains the anionic group) possess little or no useful oxygen-carrying activity.

According to an advantageous embodiment of the invention, all of the Z sites which are implicated in covalent linkages between the polymer and hemoglobin are the same as the Z sites which are implicated in the ionic linkages between the polymer and hemoglobin.

A useful class of macromolecular conjugates of hemoglobin according to the invention is constituted by those in which the covalent linkages between the polymer P and hemoglobin are established between at least one carboxylic or aldehyde or OH group borne by the Z sites and at least one amino group of hemoglobin situated in the allosteric site of hemoglobin, in particular the amino group of at least one of the two $\beta$-terminal valines of hemoglobin.

Another useful class of macromolecular conjugates of hemoglobin according to the invention is constituted by those in which the salt bridges between the $NH_3^+$ groups and the $COO^-$ groups within the hemoglobin molecule are intact when the hemoglobin is in the deoxygenated form.

Another useful class of macromolecular conjugates according to the invention is constituted by those in which the polymer P is selected from among the polysaccharides, in particular the hydroxyalkyl starches in which the alkyl radical contains from 2 to 4 carbon atoms, inulin, dextran and its derivatives, in particular aminated dextran, polyvinyl alcohol, polyvinylpyrrolidone, polymethacrylate and its derivatives, polypeptides, polyalkylene glycols in which the alkylene group contains from 2 to 2 carbon atoms, in particular polyethylene glycol and polypropylene glycol.

Another useful class of macromolecular conjugates according to the invention is constituted by those in which the polymer P has a mean molecular mass lower than or equal to 70,000, when it is constituted by dextran and its derivatives, and a molecular mass lower than or equal to 10,000 when it is chosen from among the polyalkylene glycols, polyvinylpyrrolidone or polymethylacrylate.

Another useful class of macromolecular conjugates according to the invention is constituted by those in which the Z site is linked to the polymer by the intermediary of an ester, ether, amide or amine function.

Another useful class of macromolecular conjugates according to the ivnetnion is constituted by those in which the Z site contains $OSO_3H$, $OPO_3H_2$, O—CH(COOH)$_2$, —O—CH(COOH)—CH$_2$—COOH, n varying from 1 to about 4, or is derived from pyridoxal sulfate, pyridoxal phosphate, adenosine triphosphate, phosphotyrosine, phosphoserine, inositol hexaphosphate and its derivatives, polycarboxylic acids containing from 2 to 10 carbon atoms in the main chain, benzene carboxylic acids containing at least 3 carboxylic functions, 2,3-diphosphoglycerate.

Another useful class of compounds according to the invention is constituted by those in which no ionic linkage and no covalent linkage can be formed other than those between suitable groups at the Z sites of the polymer and hemoglobin, respectively.

Another useful class of macromolecular conjugates according to the invention is constituted by those in which the covalent linkages between the polymer and hemoglobin are established with the involvement of the carboxylic groups includes in the Z sites bound to the polymer and $NH_2$ groups of hemoglobin.

Another useful class of macromolecular conjugates according to the invention is constituted by those in which the ionic linkages between the polymer P and hemoglobin are established between the carboxylate groups of the Z sites and hemoglobin.

All that has been said with regard to the macromolecular conjugates obtained starting from the new procedure described above applies in particular to the macromolecular conjugates of the invention.

The new macromolecular conjugates according to the invention can be obtained starting either from a procedure making use of oxyhemoglobin, or from a procedure making use of deoxyhemoglobin.

The hemoglobin conjugates according to the invention can be obtained in the following manner:

in the first step, Z sites containing the ionic groups destined to lead to the formation of an ionic linkage with hemoglobin are bound to polymer P in the following ratio:

when a Z site contains a unique anionic group constituted by a sulfate or a phosphate, there is at least one such Z site per polymer chain and not more than one such Z site for every eleven monomers, when a Z site contains a unique anionic group constituted by a carboxylate, not involved in linkage between the site and the polymer and not involved in covalent linkage between the polymer and hemoglobin, there is at least one such Z site per polymer chain, when a Z site contains two anionic charges derived from two carboxylates not involved in linkage between the site and the polymer and not involved in covalent linkage between the polymer and hemoglobin, there is at least one such Z site per polymer chain and not more than one such Z site for every six monomers, the polymer P being water-soluble, non-toxic, preferably non-antigenic, hemocompatible, of molecular mass of about 1,000 to about 500,000, and preferably of about 1,000 to about 100,000, containing polar groups, and preferably hydroxyl, carboxylic or amine groups, and the Z sites containing, on the one hand, at least one negative charge borne by sulfate and/or phosphate and/or carboxylate groups and containing, on the other hand, at least one carboxylic, aldehyde or OH group, either by using a compound Z-Y in which Y is an active or activatable function such as aldehyde, carboxylic, amine, hydroxyl or halogen, or by carrying out a radical grafting at the Z sites on the polymer P;

then in the second step, the polymer P containign the Z site(s) is made to react with hemoglobin in the oxygenated form in a non-deoxygenated medium under conditions such that the hemoglobin does not undergo denaturation and can pass, after coupling to the polymer, in a reversible manner from the oxygenated form to the deoxygenated form in aqueous medium at a pH varying between about 5 and about 9, in order to form, on the one hand, at least one ionic linkage between at least one of the Z sites borne by the polymer and hemoglobin and, on the other, at least one covalent linkage between the same above-mentioned Z site borne by the polymer and hemoglobin, when the reaction mentioned above may possibly lead to imine functions, these latter can be stabilized as amine functions, for example by reduction with the aid of $NaBH_4$, $NaCNBH_3$, dimethylaminoborane or HCOOH.

The conjugates according to the invention can also be obtained according to the procedure described in the French patent application No. 86.09625.

The hemoglobin conjugates irreversibly linked to polyanionic polymers prepared according to the invention can, when they are dissolved in aqueous solutions of suitable composition, play a role as blood substitutes, in particular in operations requiring transfusions or the perfusion of an organ.

Consequently, the invention also relates to aqueous solutions containing the conjugates described above and, in particular, to solutions made isotonic with blood by prolonged dialysis against a Tyrode solution (composition: NaCl 8 g/l; KCl 0.2 g/l; $CaCl_2$ 0.2 g/l; $MgCl_2$ 0.1 g/l; $NaH_2PO_4$ 0.05 g/l; $NaHCO_2$ 1 g/l; D-glucose 1 g/l) for example and concentration by ultrafiltration until a hemoglobin concentration of about 7% is obtained.

Preparations of macromolecular conjugates of hemoglobin obtained according to the invention have been examined as potential transporters of oxygen. It has been possible to show that they are in fact capable of binding oxygen reversibly and, in particular, of releasing it more readily than free hemoglobin. In fact, these preparation appear to be characterized by half-saturation pressures ($P_{50}$) which are very high (from 900 to 5,000 Pa) whereas under the same conditions (0.05M NaCl, pH 7, 25° C.) that of native hemoglobin is equal to about 430 Pa.

Thus, these conjugates can be used to supply large amounts of oxygen to ischemic tissues. They may also be used in transfusions and be administered to patients in the form of an aqueous solution made isotonic with blood, in the presence or absence of excipients.

The conjugates can also be lyophilized in the presence or absence of a protecting agent or atomized, and be redissolved in water before utilization.

The macromolecular conjugates according to the invention have been tested with respect to their acute toxicity.

The invention will be better understood with the aid of the examples which follow and which are not intended to be limiting in scope.

Example 1

Synthesis of a covalently linked conjugate of hemoglobin and dextran-benzene pentacarboxylate (M.M. of dextran 40,000). Coupling with oxyhemoglobin.

Aminated dextran containign $5 \times 10^{-4}$ moles of $NH_2$ per g of dry produce (i.e. 8 moles of $NH_2$ per 100 moles of glucopyranose) is prepared according to P. HUBERT et. al., Proc. Natl. Acad. Sci. USA, 1978, 75, 3143, by the action of ammonia on dextran activated by epichlorohydrin.

1 g of this aminated dextran is dissolved in 20 ml of water and the pH is adjusted to 6.5 with 0.1N HCl. 1.7 g of benzene hexacarboxylic acid are then added, followed by 1 g of N'-ethyl-N-(3-dimethyl-aminopropyl) carbodiimide hydrochloride (EDCI). The pH is brought to 6.5 and the reaction is allowed to proceed for three days at 20° C. After being dialyzed against a solution of 0.5M sodium acetate, the mixture is treated with acetic anhydride in order to block the unsubstituted amino functions of the dextran. Contaminants of low molecular weight are then removed by desalting the solution on a column of Ultrogel AcA 202 (IBF-France) in 0.2M phosphate buffer, pH 7.2.

After being extensively dialyzed against water, the solution containing the polyanionic polymer is lyophilized. The compound is stored in the cold in a vacuum. the dextran polycarboxylate obtained contains $2 \times 10^{-4}$ moles of benzene pentacarboxylate (B.P.C.) per g of polymer.

5 g of dextran polycarboxylate are dissolved in 250 ml of 0.05M NaCl. The pH is adjusted to 7 with 0.1N sodium hydroxide and 150 ml of a 10% hemoglobin solution re added. Subsequently, 600 mg of N'-ethyl-N-(3-dimethyl aminopropyl) carbodiimide hydrochloride (EDCI) are added and the reaction is allowed to proceed at 20° C. for 2 hours. The chromatogram obtained after filtration through a column of Ultrogel AcA 34 (IBF-France) confirms the absence of free hemoglobin. The $P_{50}$ of the conjugate is 2660 Pa (25° C., 0.05M Tris, pH=7.2; free Hb under the same conditions: $P_{50}$430 Pa).

Example 2 Synthesis of a covalently linked conjugate of hemoglobin and dextran-benzene pentacarboxylate (M.M. of dextran 10,000). Coupling with oxyhemoglobin.

The polymer is prepared from an aminated dextran containing $4 \times 10^{-4}$ moles of $NH_2$ per g of dry product, prepared in the same manner as that of Example 1.

1 g of this aminated dextran is dissolved in 20 ml of water and the pH is adjusted to 7.5 with 0.1M NaOH.

Subsequently, 0.7 g of benzene hexacarboxylic acid (B.H.C.) are then added followed by 1 g of N'-ethyl-N-(3-dimethyl-aminopropyl) carbodiimide hydrochloride (EDCI). The reaction is allowed to proceed for 1 day at 20° C. After being dialyzed against a solution of 0.5M sodium acetate, the mixture is treated with acetic anhydride in order to block the unsubstituted amine functions of the dextran. Contaminants of low molecular weight are then removed by desalting the solution on a column of Ultrogel AcA 202 (IBF France) in 0.2M phosphate buffer, pH=7.2. High performance liquid chromatography with the aid of a TSK G 3000 SW column (LKB France) confirms that the excess benzene hexacarboxylate has been completely removed from the dextran polycarboxylate.

After being extensively dialyzed against water, the solution containing the polyanionic polymer is lyophilized. The compound is stored in the cold in a vacuum. The dextran polycarboxylate obtained contains $3.5 \times 10^{-4}$ moles of B.P.C. per g of polymer.

2.5 g of dextran polycarboxylate are dissolved in 150 ml of 0.05M aqueous NaCl. 100 ml of a 10% solution of hemoglobin are added. The pH is adjusted to 7.5 with 0.1M sodium hydroxide and the volume is made up to 300 ml with 0.05M aqueous NaCl.

350 mg of EDCI are then added and the reaction is allowed to proceed at 20° C. for 2 hours. The chromatogram obtained on a TSK G 3000 SW column (LKB France) confirms the absence of free hemoglobin.

Figure 2:
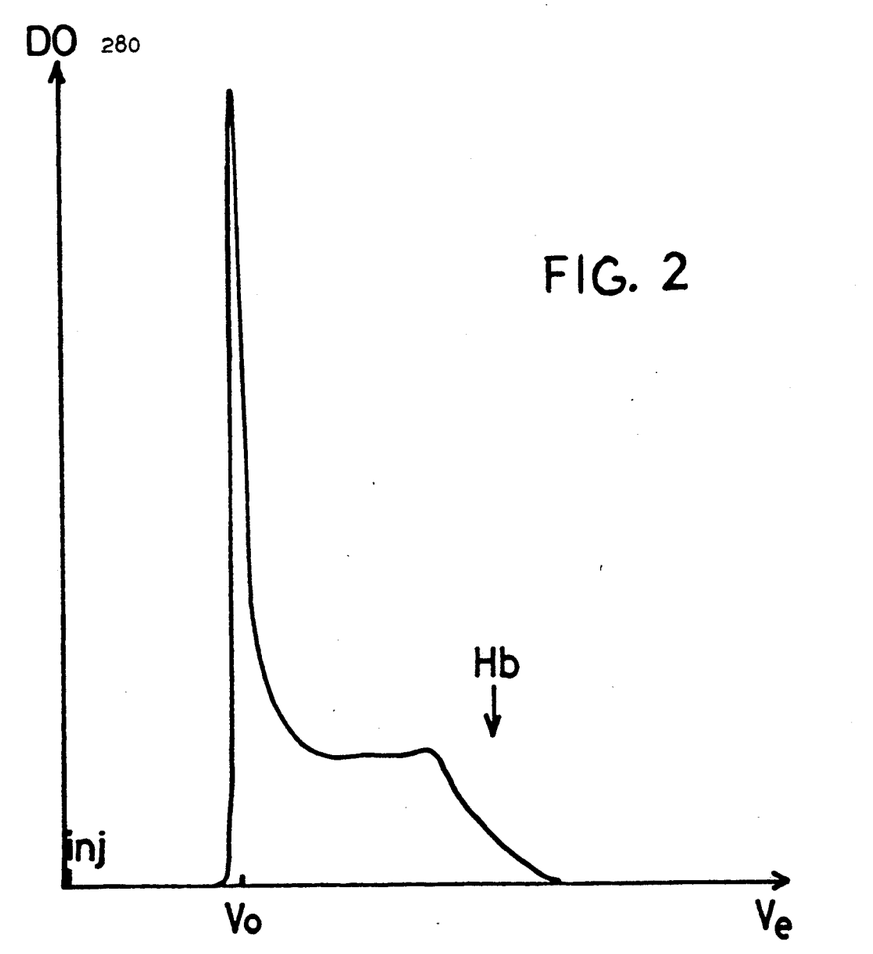
FIG. 2 graphically illustrates the variation of the optical density as a function of the elution volume for the conjugate of Example 2.

FIG. 2 shows the optical density as a function of the elution volume and demonstrates the absence of free hemoglobin. In this figure, Vo corresponds to the exclusion volume of the column and the arrow under Hb indicates the elution volume of free hemoglobin, i.e. hemoglobin not coupled to the polymer.

The $P_{50}$ of the conjugate is 2720 Pa (25° C., 0.05M Tris, pH=7.2; free Hb under the same conditions: $P_{50}$430 Pa).

Example 3

Synthesis of a covalently linked conjugate of hemoglobin and dextran-benzene tricarboxylate (M.M. of dextran 10,000). Coupling to oxyhemoglobin.

The polymer is prepared starting from an aminated dextran containign $4 \times 10^{-4}$ moles of $NH_2$ per g of dry polymer.

1 g of this aminated polymer is dissolved in 20 ml of water and the pH is adjusted to 7.5 with 0.1M NaOH. 0.5 g of 1,2,4,5-benzene tetracarboxylic acid (B.T.C.) are then added followed by 0.6 g of EDCI. The reaction is allowed to proceed for 1 day at 20° C. The solution is then treated as in Example 2.

The dextran polycarboxylate obtained contains $3.2 \times 10^{-4}$ moles of benzene tricarboxylate per g of polymer.

0.5 g of this dextran polycarboxylate are dissolved in 25 ml of 0.05M aqueous NaCl. 10 ml of a 10% solution of hemoglobin are added. The pH is adjusted to 7.5 with 0.1M sodium hydroxide and the volume is made up to 40 ml with 0.05M aqueous NaCl.

Figure 3:
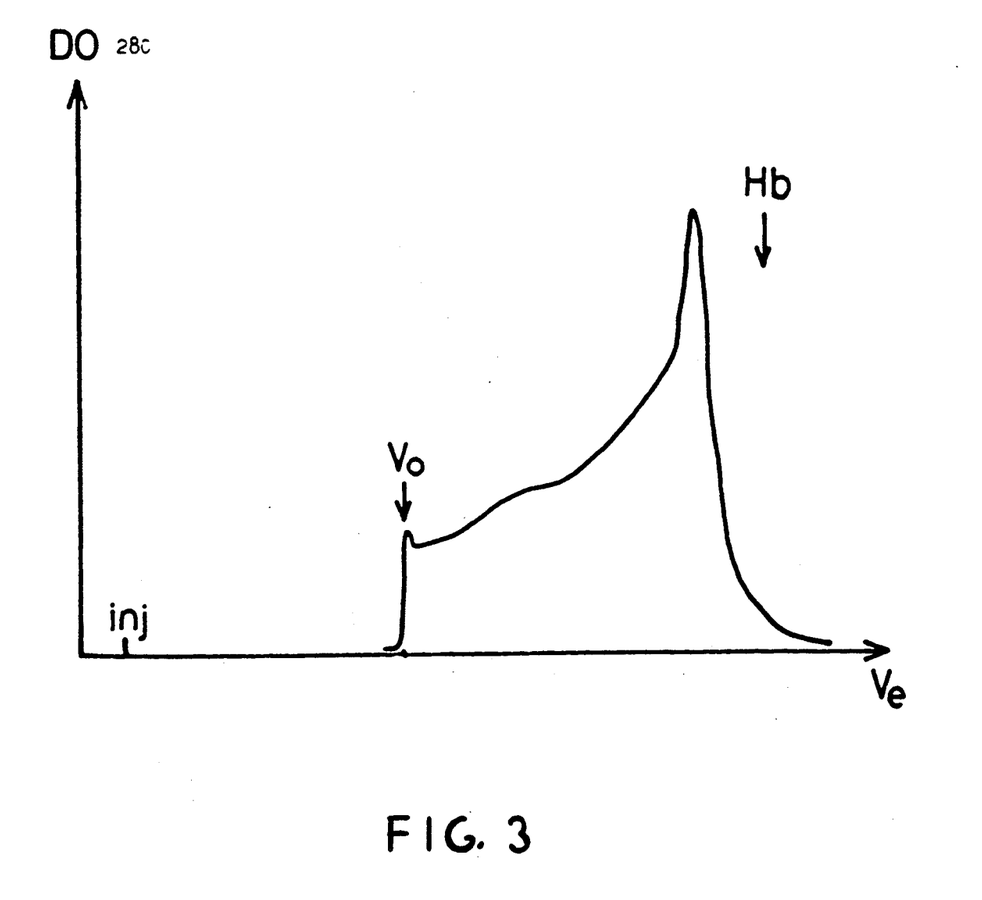
FIG. 3 shows the optical density as a function of the elution volume of the conjugate of Example 3.

50 mg of EDCI are then added and the reaction is allowed to proceed at 20° C. for 2 hours. The chromatogram obtained on a TSK G 3000 SW column (LKB France) confirms the absence of free hemoglobin. FIG. 3 shows the optical density as a function of the elution volume and demonstrates the absence of free hemoglobin. In this figure, the arrow under Vo corresponds to the exlusion volume of the column and the arrow under Hb indicates the elution volume of free, i.e. uncoupled, hemoglobin.

The $P_{50}$ of the conjugate is 710 Pa (25° C., 0.05M Tris, pH=7.2; free Hb under the same conditions: $P_{50}$=430 Pa).

Example 4

Synthesis of a covalently linked conjugate of hemoglobin and dextran-butane tricarboxylate (M.M. of the dextran 10,000). Coupling to oxyhemoglobin.

The polymer is prepared in the same manner as that of Example 3 by using 1,2,3,4-n-butane tetracarboxylic acid (Bu.T.C.). The dextran polycarboxylate obtained contains $4 \times 10^{-4}$ moles of butane tricarboxylate per g of polymer.

0.6 g of this dextran polycarboxylate are dissolved in 25 ml of 0.05M aqueous NaCl. 10 ml of a 10% solution of hemoglobin are added. The pH is adjusted to 7.5 with 0.1M sodium hydroxide and the volume is made up to 40 ml with 0.05M aqueous NaCl.

70 mg of EDCI are then added and the reaction is allowed to proceed at 20° C. for 2 hours. The chromatogram obtained on a TSK G 3000 SW column (LKB France) confirms the absence of free hemoglobin. The $P_{50}$ of the conjugate obtained is 540 Pa (25° C., 0.05M Tris, pH=7.2; free hemoglobin under the same conditions: $P_{50}$=430 Pa).

Example 5 Synthesis of a covalently linked conjugate of hemoglobin and monomethoxypolyoxyethylene-benzene pentacarboxylate (M.M. of the polyoxyethylene: 5000). Coupling with oxyhemoglobin.

Aminated monomethoxypolyoxyethylene (MPOE—NH$_2$, $2 \times 10^{-4}$ moles of NH$_2$ per g of dry product) is prepared according to M. LEONARD et al., Tetrahedron 1984, 40, 1581, by the action of thionyl bromide on MPOE, followed by substitution with ammonia.

2 g of this MPOE—NH$_2$ are dissolved in 50 ml of water and the pH is adjusted to 8. Subsequently, 1.4 g of benzene hexacarboxylic acid (B.H.C.) are added, followed by 0.8 g of N'-ethyl-N-(3-dimethyl aminopropyl) carbodiimide hydrochloride (EDCI). The reaction is allowed to proceed overnight at ambient temperature. The mixture is then acidified to Ph 1 with 1M aqueous HCl; the polymer is extracted with methylene chloride, then precipitated with anhydrous ether.

It is then purified by chromatography on a Dowex column, and then on a column of Ultrogel AcA 202 IBF, France). The eluate is dialyzed against aqueous sodium hydroxide (pH 9), then the polymer is lyophilized.

Figure 4:
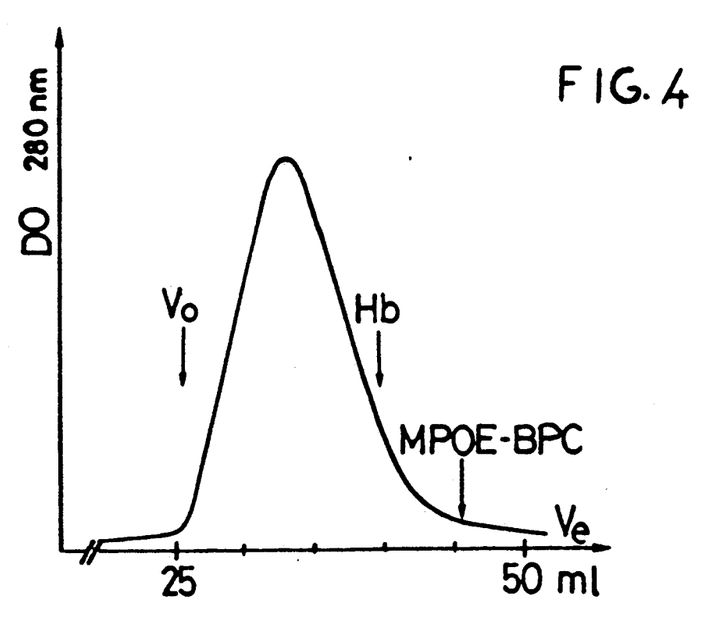
FIG. 4 graphically illustrates the variation of the optical density as a function of the elution volume of the conjugate of Example 5.

0.2 g of this polymer containing about $1.5 \times 10^{-4}$ moles of benzene-pentacarboxylate (B.P.C.) per g of polymer are dissolved in 10 ml of water. The pH is adjusted to 7 and 10 ml of a 10% solution of hemoglobin are added, followed by 10 mg of EDCI. After a reaction time of one hour, the mixture is chromatographed on a column of Ultrogel AcA 54 (IBF, France) in order to purify the polymeric conjugate of hemoglobin. FIG. 4 shows the variation of the optical density of the function of the elution volume and demonstrates the absence of free hemoglobin. Vo corresponds to the exclusion volume of the column; the arrow under Hb indicates the elution volume of free, i.e. uncoupled, hemoglobin, and that under MPOE-BPC corresponds to the elution volume of the polymer not bound to hemoglobin. The $P_{50}$ of this conjugate is 2400 Pa (25° C. 0.05M Tris, pH 7.2; free Hb under the same conditions: $P_{50}$=430 Pa).

Example 6

Synthesis of a covalently linked conjugate of hemoglobin and dextran-benzene dicarboxylate (M.M. of the dextran 10,000: ester linkage between the dextran and the polycarboxylate site). Coupling with oxyhemoglobin.

The dextran-benzene dicarboxylate is prepared by reacting 7.5 g of benzene 1,2,4-tricarboxylic acid anhydride with 32 g of dextran in aqueous medium at pH 9 for 15 h. Residual benzene 1,2, 4-tricarboxylic acid is then removed from the solution by desalting on a column of Ultrogel AcA 202 (IBF-France) with a 0.2M phosphate buffer, pH 7.2.

After being dialyzed extensively against water, the solution containing the polymer is lyophilized. The dextran polycarboxylate contains $6.3 \times 10^{-4}$ moles of benzene dicarboxylate (B.D.C.) per g of polymer.

This corresponds to about 1 Z site containign two anionic groups constituted by two carboxylate groups for every ten monomers.

11 g of dextran polycarboxylate are dissolved in 250 ml of water. The pH is adjusted to 6.5 and 150 ml of a 10% solution of hemoglobin are added. 160 mg of N'-ethyl-N-(3-dimethylaminopropyl) carbodiimide hydrochloride (EDCI) are then added and the reaction is allowed to proceed at 20° C. for 2 hours.

The hemoglobin conjugate obtained is a new conjugate.

The mixture is chromatographed on Ultrogel AcA 54 IBF France) in order to remove free hemoglobin and contaminants. The $P_{50}$ of the purified conjugate is 870 Pa (25° C., 0.05M Tris, pH 7.2; free Hb under the same conditions: $P_{50}$=430 Pa.).

Example 7

Synthesis of a covalently linked conjugate of hemoglobin and dextran-benzene tricarboxylate (M.M. of the dextran 10,000: ester linkage between the dextran and the polycarboxylate site). Coupling with oxyhemoglobin.

The dextran-benzene tricarboxylate is prepared by reacting 26 g of benzene 1,2,4,5-tetracarboxylic acid dianhydride with 20 g of dextran in aqueous medium at pH 9 for 15 h. Residual benzene 1,2,4,5-tetracarboxylic acid is then removed from the solution by desalting on a column of Ultrogel AcA 202 (IBF-France) with a 0.2M phosphate buffer, pH 7.2.

After being extensively dialyzed against water, the solution containing the polymer is lyophilized. The dextran polycarboxylate contains $1.15 \times 10^{-3}$ moles of benzene tricarboxylate (B.T.C.) per g of polymer.

5 g of dextran polycarboxylate are dissolved in 250 ml of water. The pH is adjusted to 7.0 and 150 ml of a 10% solution of hemoglobin are added. 120 mg of N'-ethyl-N-(3-dimethylaminopropyl) carbodiimide hydrochloride (EDCI) are then added and the reaction is allowed to proceed at 20° C. for 2 hours.

The mixture is chromatographed on Ultrogel AcA 54 (IBF France) in order to remove free hemoglobin and contaminants. The $P_{50}$ of the purified conjugate is 2000 Pa (25° C., 0.05M Tris, pH 7.2; free Hb under the same conditions: $P_{50}$=430 Pa).

The conjugate specified above can also be prepared with the aid of dextran and benzene 1,2,4,5-tetracarboxylic acid in the presence of a carbodiimide soluble in water such as N'-ethyl-N-(3-dimethylaminopropyl) carbodiimide hydrochloride (EDCI).

Example 8

The following conjugates are prepared according to the procedure described in Example 5:
  hemoglobin and polyethylene glycol-benzene pentacarboxylic
  hemoglobin and polyethylene glycol-benzene tetracarboxylic
  hemoglobin and polyethylene glycol-benzene tricarboxylic
  hemoglobin and polyethylene glycol-benzene dicarboxylic

Example 9

The conjugate of hemoglobin and polyethylene glycol-benzene tricarboxylic is prepared according to the procedure described in the Examples 6 and 7.

In order to prepare polyethylene glycol-benzene tricarboxylic, benzene tetracarboxylic acid dianhydride is made to react with polyethylene glycol in an organic medium such as dimethylformamide. Residual benzene tetracarboxylic acid is then removed from the solution by, for example, desalting on a column of Ultrogel AcA 202 (IBF-France) with 0.2M phosphate buffer, pH 7.2.

After being extensively dialyzed against water, the solution containing the polymer is lyophilized.

The polyethylene glycol polycarboxylate is dissolved in water. The pH is adjusted to 7.0 and 10% solution of hemoglobin is added. Then N'-ethyl-N-(3-dimethylaminopropyl) carbodiimide hydrochloride (EDCI) is added and the reaction is allowed to proceed at 20° C. for 2 hours.

The mixture is chromatographed on Ultrogel AcA 54 IBF France) in order to remove free hemoglobin and contaminants.

The conjugate of hemoglobin and polyethylene glycol-benzene dicarboxylic (using polyethylene glycol and benzene 1,2,4-tricarboxylic acid anhydride) is also prepared according to the protocol previously mentioned.

Polyethylene glycols-benzene polycarboxylates can also be prepared by reacting the benzene polycarboxylic acids with the OH functions of the polymer in the presence of dicyclohexylcarbodiimide/dimethylaminopyridine in dimethylformamide.

COMPARATIVE EXAMPLE 1

The purpose of this example is to compare the $P_{50}$ obtained by making use of the procedure of the invention to prepare hemoglobin conjugates in which the covalent bond is established through an aldehyde group not carried at the Z site on which a phosphate anionic group is located.

The dextran phosphate is prepared using a starting dextran of molecular mass of about 10,000 which is transformed into the disodium phosphate containing 8% phosporus in conformity with the procedure described in Example 1 of the French patent application No. 86.09625.

The dextran phosphate is activated by sodium periodate so as to produce 13 aldehydes per 100 glucosidic units.

This aldehydic dextran phosphate is made to react with hemoglobin in the proportion 1.56 by weight (weight of dextran/weight of hemoglobin), at pH 8; the reaction is allowed to proceed at 4° C. for 24 h. A solution of $NaBH_4$ in $10^{-3}N$ NaOH is then added. The mixture is chromatographed to confirm the absence of free hemoglobin (HPLC on a TSK G 3000 SW column, Beckmann).

when the reaction is carried out on deoxyhemoglobin according to the procedure described in the French patent application No. 86.09625, the $P_{50}$ of the hemoglobin conjugate is 3380 Pa (25° C., 0.05M Tris, pH 7.2).

Under the same conditions, the $P_{50}$ of free hemoglobin is 450 Pa.

When the reaction is carried out on oxyhemoglobin, in conformity with the procedure of the rpesent invention, the $P_{50}$ of the hemoglobin conjugate is 425 Pa (25° C., 0.05M Tris, pH 7.2).

Under the same conditions, the $P_{50}$ of free hemoglobin is 430 Pa.

This comparative example shows that the procedure for the preparation of hemoglobin conjugates using oxygenated hemoglobin is not applicable when the covalent linkage is established between an aldehyde group (carboxylic or OH group) not bound to the Z site containing the anionic charges.

We claim:

1. A process for making a conjugate comprising the steps of:
    a) providing a hemoglobin which can undergo a reversible transition between the oxygenated state and a deoxygenated state and a water-soluble hemocompatible polymer which can covalently and ionically bond to the hemoglobin, wherein the polymer has a molecular weight of about 1,000 to 500,000 daltons and has a chemically bonded ligand with i) at least one negative charge borne by an anionic group comprising a sulfate, phosphate or carboxylate moiety which forms an ionic bond with an amino group at an allosteric site on the hemoglobin and ii) at least one polar group selected from the group comprising a hydroxyl, carboxyl or aldehyde moiety which forms a covalent bond between the polymer and the hemoglobin; and wherein the conjugate has a mean molecular weight of about 70,000 to 1,000,000 daltons and salt bridges between internal $NH_3^+$ and $COO^-$ groups of the hemoglobin being intact when the hemoglobin is in the deoxygenated state; and
    b) reacting the polymer with the hemoglobin in the oxygenated state in a non-deoxygenated aqueous medium at a pH of about 5 to 9 to form simultaneously the ionic bond and the covalent bond between the hemoglobin and the ligand on the polymer without denaturing the hemoglobin.

2. The process of claim 1, wherein imine groups on the conjugate are subsequently stabilized by being reduced to amine groups.

3. The process of claim 2, wherein the imine groups are reduced with $NaBH_4$, $NaCNBH_3$, dimethylaminoborane or HCOOH.

4. The process of claim 1, wherein the conjugate comprises a plurality of the ligands on the polymer and wherein:
    when each ligand has chemically bound an anionic group which comprises sulfate or phosphate moiety, there is at least one ligand for every ten monomers of the polymer;
    when each ligand has chemically bound at least two anionic groups which comprises sulfate and/or phosphate moiety, there is at least one such ligand on the polymer;
    when each ligand has chemically bound the anionic group which comprises carboxylate moieties, there are at least two carboxylate moieties on each ligand and there is at least one ligand for every five monomers; and
    when at least one of the ligands has chemically bound at least three anionic groups which comprises carboxylate moieties, there is at least one such ligand on the polymer.

5. The process of claim 1, wherein the conjugate comprises a plurality of the ligands on the polymer and wherein:

when a ligand has chemically bound an anionic group which comprises a sulfate or phosphate moiety, there is at least one ligand on the polymer and not more than one ligand for every eleven monomers of the polymer;

when a ligand has chemically bound an anionic group which comprise a carboxylate moiety not involved in the covalent linkage between the polymer and the hemoglobin, here is at least one ligand on the polymer; and when a ligand has chemically bound two anionic groups which comprise two carboxylate moieties not involved in the linkage between the ligand and the polymer and not involved in the covalent linkage between the polymer and the hemoglobin, there is at least one ligand per polymer and not more than one such ligand for every six monomers.

6. The process of claim 1, wherein the covalent bond between the polymer and the hemoglobin is between a carboxyl, aldehyde or hydroxyl group on the ligand and at least one allosteric amino group of the hemoglobin in a deoxygenated form.

7. The process of claim 6 wherein the allosteric amino group is an amino group of at least one of the two β terminal valines of the hemoglobin.

8. The process of claim 1, wherein the polymer is a polysaccharide, polyvinyl alcohol, polyvinylpyrrolidone, polymethacrylate, polypeptide and polyalkylene glycol.

9. The process of claim 8, wherein the polymer is hydroxylalkyl starch in which the alkyl is of 2 to 4 carbon atoms, inulin, dextran, an aminated dextran or a polyalkylene glycol in which the alkylene is of 2 to 5 carbon atoms.

10. The process of claim 9, wherein the polymer is a dextran having a mean molecular weight of no more than 70,000 daltons.

11. The process of claim 10, wherein the polymer is a polyalkylene glycol, polyvinylpyrrolidone or polymethacrylate having a mean molecular weight of no more than 10,000 daltons.

12. The process of claim 1, wherein the ligand is chemically bound to the polymer by an ester, amide or amine linkage.

13. The process of claim 1, wherein the ligand is a $-OSO_3H$, $-OPO_3H_2$, $-O-CH(COOH)_2$, $-O-(-COOH)-CH_2-COOH$, or n varying from 1 to 4 or is a pyridoxalsulfate, pyridoxalphosphate, adenosine triphosphate, phosphotyrosine, phosphoserine, inositol hexaphosphate, polycarboxylic acid of 2 to 10 carbon atoms in the main chain, benzene carboxylic acid containing at least three carboxylic functions or 2,3-diphosphoglycerate.

14. The process of claim 1 wherein the polymer is selected form the group consisting of: aminated dextran of molecular mass of about 40,000 and about $2 \times 10^{-4}$ moles of benzene hexacarboxylic acid per gram of dextran; aminated dextran of molecular mass of about 10,000 and about $3.5 \times 10^{-4}$ moles of benzene hexacarboxylic acid per gram of dextran; aminated dextran of molecular mass of about 10,000 and about $3.2 \times 10^{-4}$ moles of benzene tetracarboxylic acid per gram of dextran; aminated dextran of molecular mass of about 10,000 and about $4 \times 10^{-4}$ moles of butane tetracarboxylic acid per gram of polymer; aminated monomethoxypolyoxyethylene of molecular mass of about 5,000 and about $1.5 \times 10^{-4}$ moles of benzene hexacarboxylic acid per gram of polymer; and dextran of molecular mass of about 10,000 and about $1.15 \times 10^{-3}$ moles of 1,2,4,5-benzene tetracarboxylic acid per gram of polymer.

15. The process of claim 1 wherein, after step a) the polymer is activate before step b).

16. The process of claim 15, wherein the polymer is activated by converting a hydroxyl moiety into an aldehyde moiety.

17. The process of claim 16, wherein the hydroxyl moiety is converted into an aldehyde moiety by a periodate oxidation.

18. The process of claim 15, wherein the activation of the polymer and its reaction with hemoglobin in step b) are practically simultaneous.

19. The process of claim 15, wherein the ligand is activated using carbonyl diimidazole when the ligand does not contain an aldehyde moiety but does contain a hydroxy moiety or is activated using reagents for peptide synthesis when the ligand contains a carboxyl moiety.

20. The process of claim 1, wherein the reaction between the polymer and hemoglobin is carried out for a length of time such that no more than about 5% of methemoglobin is formed.

21. The process of claim 20, wherein the reaction between the polymer and the hemoglobin does not exceed 10 hours in length and is at a temperature at which the hemoglobin is not denatured.

22. The process of claim 1, wherein the ligand is linked to the polymer by an ester linkage; an anhydride of the ligand being reacted with the polymer containing hydroxyl moieties in a medium in which the polymer is soluble in order to bind the ligand to the polymer.

23. The process of claim 22, wherein the anhydride of the ligand is 1,2,4,5-benzene tetracarboxylic acid dianhydride or 1,2,4-benzene tricarboxylic acid anhydride and the polymer is a dextran or a polyethylene glycol.

* * * * *